United States Patent [19]

Matthiessen

[11] Patent Number: 4,988,429
[45] Date of Patent: Jan. 29, 1991

[54] MEASURING CELL FOR AN ELECTROCHEMICAL GAS SENSOR

[75] Inventor: Hans Matthiessen, Bad Schwartau, Fed. Rep. of Germany

[73] Assignee: Drägerwerk Aktiengesellschaft, Lübeck, Fed. Rep. of Germany

[21] Appl. No.: 544,107

[22] Filed: Jun. 22, 1990

[30] Foreign Application Priority Data

Jun. 30, 1989 [DE] Fed. Rep. of Germany ....... 3921526

[51] Int. Cl.$^5$ .......................................... G01N 27/40
[52] U.S. Cl. ................................... 204/408; 204/415
[58] Field of Search ............................. 204/408, 415

[56] References Cited

U.S. PATENT DOCUMENTS 4,338,174 7/1982 Tamura ............................. 204/408

FOREIGN PATENT DOCUMENTS 2094005 9/1982 United Kingdom .

OTHER PUBLICATIONS

G. Voorn et al., Science and Industry, No. 16, pp. 49-50 (1980).

Primary Examiner—G. L. Kaplan
Attorney, Agent, or Firm—Walter Ottesen

[57] ABSTRACT

The invention is directed to a measuring cell for an electrochemical gas sensor having an electrolytic chamber and a measuring electrode as well as a counter electrode. In the direction facing the ambient, the measuring electrode includes a diffusion membrane as well as a diffusion barrier. The diffusion barrier is made of a material which is a good conductor of heat and is provided with a plurality of passages. A temperature-sensitive element is provided in the immediate proximity of these passages and faces toward the ambient. With this configuration, the temperature dependency of the diffusion capacity of the gas sample passing through the diffusion barrier can be included in the processing of the signal indicative of the measurement.

7 Claims, 1 Drawing Sheet

MEASURING CELL FOR AN ELECTROCHEMICAL GAS SENSOR

FIELD OF THE INVENTION

The invention relates to a measuring cell for an electrochemical gas sensor having a housing defining an electrolytic chamber which accommodates at least one measuring electrode and a counter electrode. A porous membrane is mounted in the housing and separates the chamber from the ambient to be investigated and contains the electrolyte in the chamber. The porous membrane is permeable to the gaseous substance to be detected. The measuring cell also includes a diffusion barrier mounted in the housing so as to be interposed between the ambient and the membrane and includes passages for passing the gaseous substance to the porous membrane.

BACKGROUND OF THE INVENTION

A measuring cell of the kind described above is disclosed in published British patent application No. 2,094,005.

The known measuring cell operates according to the amperometric principle pursuant to which the gas molecules diffusing through the membrane initiate an electrochemical reaction in the electrolyte. This reaction is processed to a measuring signal via the measuring tap on the electrodes. The conversion rate of the gas sample is dependent on temperature so that the sensitivity of the sensors can change with the temperature. This temperature dependency is often also dependent on the age of the sensors and also for the same types of sensors; that is, the temperature dependency can be different from one measuring cell to the next where the sensor configuration (electrolyte and electrode material) is suitable for detecting a specific type of gas.

For obtaining a constant sensitivity, it is known to heat the sensors and to hold the same at a constant temperature. However, this method has the disadvantage that the energy needed therefor, for example, in portable gas measuring apparatus must be supplied by a battery and therefore is limited.

A further known method includes mounting a temperature sensor at a suitable location and processing the temperature signal thereof either in an analog manner in a preamplifier or digitally in a software supported microprocessor while correspondingly compensating the measuring signal (temperature compensation method). In this method, it is disadvantageous that the temperature sensor cannot be mounted in the direct vicinity of the subassembly causing the temperature movement. This subassembly comprises the porous membrane, the catalytic measuring electrode and the electrolyte. A thermal coupling of the temperature sensor to this subassembly is only partially achieved.

Unavoidable temperature gradients are produced by large temperature jumps since the portable apparatus are utilized at different changing locations. These temperature gradients lead to impermissible deviations since a temperature compensation within the measuring cell takes a substantially longer time duration than is required for the measuring operation itself. The measuring operation is carried out with a measuring cell in these cases which is not in thermal equilibrium to the temperature of the gas to be measured. For known measuring cells, a diffusion barrier is interposed over the membrane in the direction facing toward the ambient. This diffusion membrane on the one hand moderates the flow of the sample of the gas to be measured while, on the other hand, is intended to provide a limitation of the diffusion flow because of its configuration in combination with the characteristics of the measuring cell.

SUMMARY OF THE INVENTION

In a diffusion limiting measuring arrangement, the most significant factor influencing the obtainment of an adequately high measuring accuracy is the temperature dependency of the diffusion through the diffusion barrier. Accordingly, it is an object of the invention to provide a measuring cell of the kind described above which is improved so that the temperature dependency of the diffusion capacity of the gas sample through the diffusion barrier can be included in the processing of the signal.

The measuring cell of the invention is for an electrochemical gas sensor for detecting a gaseous substance. The measuring cell includes: a housing having an opening directed toward the sample to be measured and defining an electrolyte chamber; an electrolyte contained in the chamber; a measuring electrode and a counter electrode disposed in the chamber so as to be in spaced relationship to each other; a porous membrane mounted in the housing for separating the chamber from the ambient to be investigated and to contain the electrolyte in the chamber; the membrane being permeable to the gaseous substance to be detected; a diffusion barrier made of a material having a good thermal conductivity and being mounted in the housing so as to be interposed between the ambient and the membrane; the diffusion barrier having a surface facing the ambient and having passage means formed therein for passing the gaseous substance to the porous membrane; and, temperature-sensitive means formed on the surface in close proximity to the passage means for detecting temperature where the gaseous substance diffuses through the diffusion barrier.

The diffusion barrier is directly subjected to the ambient air and is subjected to temperature changes. With the above arrangement of the measuring cell according to the invention, it is the diffusion barrier which is the first to assume the temperature of the ambient and the measuring cell itself must not already have assumed this temperature. Even if the temperature barrier has not taken on the ambient temperature, the gas diffusing therethrough can take on the temperature of the disc defining the diffusion barrier by appropriately configuring the passages therethrough; that is, by providing substantially larger pass-through lengths in comparison to their diameter. In this way, the diffusion rate is determined by the disc temperature. The temperature-sensitive element in this way detects the "diffusion temperature" which is the only variable which is significant for the diffusion rate at the location of the diffusion barrier.

This diffusion temperature can be applied to correct the measuring signal by appropriate signal processing in the evaluation apparatus. In this way, a gas sensor is obtained having a measuring signal independent of the temperature of the gas to be measured. The temperature compensation can be reliably carried out with simple means. The temperature-sensitive element is placed directly at the location of the temperature influence for the diffusion rate. Accordingly, it is unnecessary to design the remaining parts of the measuring cell with respect to good heat conductivity and can, for this reason, utilize proven and cost-effective housings made of plastic which are simple to manufacture It is advantageous to apply the temperature-sensitive element as a layer on the diffusion barrier so that it defines a path guided around the passages of the diffusion barrier. This makes it possible to detect temperature in an encompassing manner which is integrated over the entire surface of the diffusion barrier. In this way, the number and arrangement of the passages suitable for the course of the diffusion can be determined and the temperature-sensitive layer can be arranged around the passages and even between the passages.

An especially simple embodiment of the temperature-sensitive layer is achieved by applying the layer onto the diffusion barrier as a continuous layer with at least a portion of the passages being covered. The layer is then provided with breakthroughs which are arranged so as to be aligned with the passages in the diffusion barrier. In this way, the temperature-sensitive layer is configured as part of the diffusion barrier and passages as well as breakthroughs act as diffusion paths for the gas to be measured. This provides a still more intimate connection of the temperature sensitivity with the diffusion capacity of the gas.

According to another embodiment of the invention, the diffusion barrier is made of ceramic and the temperature-sensitive element is produced from a negative temperature coefficient layer (NTC-layer). The passages in the ceramic disc are, for example, bored by a laser. An NTC-network can be applied around these passages using thick-film technology. Soldering pads are connected at the periphery of this network to facilitate bonding of connecting leads thereto.

According to another embodiment of the invention, the diffusion barrier can be in the form of a thin silicon disc having a plurality of small passages formed therein, for example, by boring the same with a laser or etching the bores into the disc. At the same time, a temperature sensor is applied using semiconductor-silicon technology.

In a further embodiment of the invention, the diffusion barrier is made of metal and carries an electrically-insulating intermediate layer. A temperature-sensitive element in the form of an NTC-layer is applied to this intermediate layer. The electrically insulating layer can be a glass layer which is applied to the metal diffusion barrier utilizing thick-film technology. The NTC-layer is applied to this glass layer by using thick-film or thin-film technology. The diameter of the passages can be generated with suitable known processing techniques such as heavy-ion bombardment in combination with etching processes in the micrometer range.

The sensitivity of the sensor is essentially determined by the diffusion barrier when the number and size of the passages are so selected that the diffusion rate of the gas sample to be measured through the passages is significantly less than the consumption caused by the activity of the measuring electrode.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
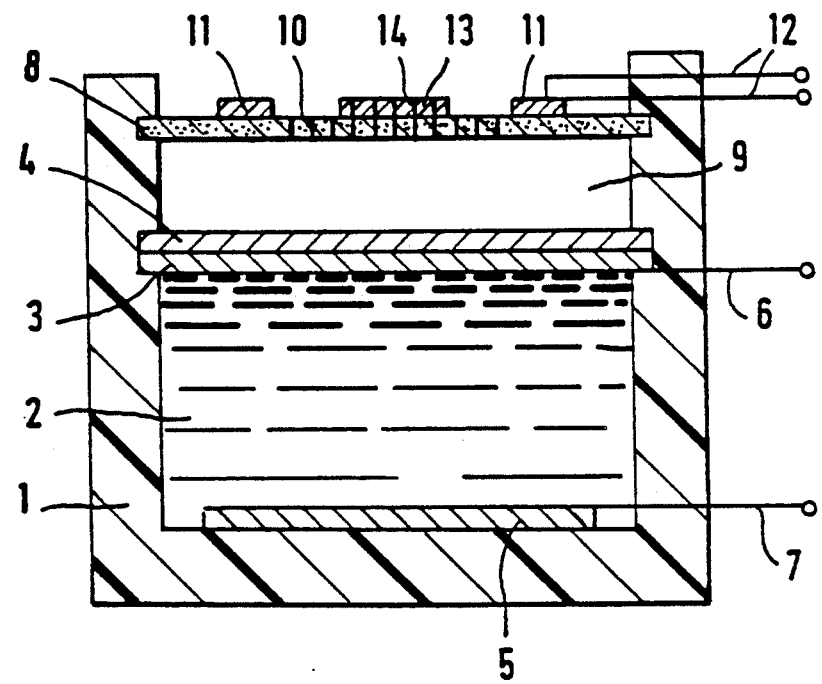
FIG. 1 is a side elevation not to scale of a measuring cell of a gas sensor according to the invention; and, FIG. 2 is a section view of a portion of a diffusion barrier according to another embodiment of the measuring cell of the invention.

The measuring cell shown in FIG. 1 includes a housing 1 defining an electrolyte chamber 2 filled with an electrolyte. In the electrolyte chamber 2, a measuring electrode 3 is provided on the side of a diffusion membrane 4 facing toward the electrolyte. A counter electrode 5 is also provided in the electrolyte chamber 2 and is spaced from the measuring electrode 3. The electrodes (3, 5) include respective measuring leads (6, 7) which are passed through the housing 1 and are connected to an evaluation apparatus (not shown). The ambient contains the gas to be investigated and the diffusion membrane 4 is separated from the ambient by a diffusion barrier 8 made of aluminum oxide ceramic. A measuring cell pre-chamber 9 is disposed between the diffusion barrier 8 and the diffusion membrane 4.

Small passages are bored or etched through the diffusion barrier 8 and are represented schematically by short vertical lines 10 because of their small dimensions.

A plurality of paths 11 of a temperature-sensitive element are vapor deposited onto the diffusion barrier 8 so as to face toward the ambient. The paths 11 have any desired wound and intertwined configuration and surround the passages 10. The paths 11 are provided with connecting leads 12 which likewise are passed through the housing 1 and connected to the evaluation apparatus (not shown). A portion of the temperature-sensitive element partially covers a region of the passages 10 on the diffusion barrier 8. In this region 13 of the temperature-sensitive layer, breakthroughs 14 are provided which are in alignment with the passages 10.

Figure 2:
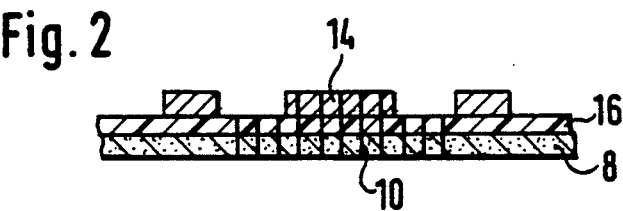

FIG. 2 shows an alternate embodiment of the diffusion barrier 8 wherein an intermediate electrically-insulating layer 16 is applied to the surface of the diffusion barrier 8. A temperature-sensitive layer is, in turn, applied to the electrically-insulating layer as shown.

It is understood that the foregoing description is that of the preferred embodiments of the invention and that various changes and modifications may be made thereto without departing from the spirit and scope of the invention as defined in the appended claims.

What is claimed is:

1. A measuring cell for an electrochemical gas sensor for detecting a gaseous substance, the measuring cell comprising:

a housing having an opening directed toward the sample to be measured and defining an electrolyte chamber;

an electrolyte contained in said chamber;

a measuring electrode and a counter electrode disposed in said chamber so as to be in spaced relationship to each other;

a porous membrane mounted in said housing for separating said chamber from the ambient to be investigated and to contain said electrolyte in said chamber;

said membrane being permeable to the gaseous substance to be detected;

a diffusion barrier made of a material having a good thermal conductivity and being mounted in said housing so as to be interposed between the ambient and said membrane;

said diffusion barrier having a surface facing the ambient and having passage means formed therein for passing the gaseous substance to said porous membrane; and, temperature-sensitive means formed on said surface in close proximity to said passage means for detecting the temperature where the gaseous substance diffuses through the diffusion barrier.

2. The measuring cell of claim 1, said passage means being a plurality of passages extending through said diffusion barrier; and, said temperature-sensitive means being a strip-shaped layer applied to said surface of said diffusion barrier so as to define a path guided around said passages.

3. The measuring cell of claim 2, said diffusion barrier being made of ceramic.

4. The measuring cell of claim 1, said passage means being a plurality of passages extending through said diffusion barrier; and, said temperature-sensitive means being a layer applied to said surface of said diffusion barrier so as to cover over at least a portion of said passages; and, said layer having breakthroughs formed therein so as to be in alignment with the passages of said portion of said passages.

5. The measuring cell of claim 4, said diffusion barrier being made of ceramic.

6. The measuring cell of claim 1, said diffusion barrier being made of ceramic and said temperature-sensitive means being a temperature-sensitive layer applied to said surface of said diffusion barrier.

7. The measuring cell of claim 1, said diffusion barrier being made of metal; and, said temperature-sensitive means including: an intermediate electrically-insulating layer applied to said surface of said diffusion barrier; and, temperature-sensitive layer means applied to said electrically-insulating layer.

* * * * *